United States Patent
Hudson et al.

(10) Patent No.: US 8,431,701 B2
(45) Date of Patent: Apr. 30, 2013

(54) PROCESS FOR THE REDUCTIVE ALKYLATION OF NORMORPHINANS

(75) Inventors: Edmund C. Hudson, Clayton, MO (US); Sharon Woods, Florissant, MO (US)

(73) Assignee: Mallinckrodt LLC, Hazelwood, MO (US)

(*) Notice: Subject to any disclaimer, the term of this patent is extended or adjusted under 35 U.S.C. 154(b) by 396 days.

(21) Appl. No.: 12/706,909

(22) Filed: Feb. 17, 2010

(65) Prior Publication Data

US 2010/0210843 A1 Aug. 19, 2010

Related U.S. Application Data

(60) Provisional application No. 61/153,021, filed on Feb. 17, 2009.

(51) Int. Cl.
*C07D 489/00* (2006.01)
*C07D 221/28* (2006.01)

(52) U.S. Cl.
USPC .............................................. 546/44; 546/74

(58) Field of Classification Search .................... 546/44, 546/74
See application file for complete search history.

(56) References Cited

U.S. PATENT DOCUMENTS

| 2,578,787 A | 12/1951 | De Benneville |
| 2008/0045715 A1 | 2/2008 | Mitchell et al. |

FOREIGN PATENT DOCUMENTS

| WO | WO 2007/083839 A1 | 7/2007 |
| WO | WO 2007/137785 A2 | 12/2007 |
| WO | WO 2009/012005 A1 | 1/2009 |

OTHER PUBLICATIONS

Grant & Hackh's Chemical Dictionary (5th Ed. 1987) at p. 148.*
De Benneville et al., "The Behavior of aliphatic Aldehydes in the Leuckart-Wallach Reaction", J. Am. Chem. Soc., 1950, 72, pp. 3073-3075.

* cited by examiner

*Primary Examiner* — Samantha Shterengarts

(57) ABSTRACT

The invention provides a process for the N-alkylation of normorphinan compounds to produce N-alkylated morphinan compounds. In particular, the process relates to the alkylation of a normorphinan compound by a carboxaldehyde in the presence of a reducing agent to form an N-alkylated morphinan.

20 Claims, No Drawings

PROCESS FOR THE REDUCTIVE ALKYLATION OF NORMORPHINANS

CROSS REFERENCE TO RELATED APPLICATIONS

This application claims the benefit of U.S. Provisional Application No, 61/153,021 filed Feb. 17, 2009, which is incorporated herein in its entirety.

FIELD OF INVENTION

The present invention generally relates to a method for the synthesis of N-alkylated morphinans. In particular, the process provides a method for reducing an iminium salt formed from the reaction of a normorphinan and a carboxaldehyde.

BACKGROUND OF THE INVENTION

N-alkylated morphinans are important pharmaceuticals, typically used as analgesics, opiate agonists, and opiate antagonists. With the increasing use of these agents, a practical and effective method of preparation of these compounds is vital to synthesizing diverse N-alkyl substituted morphinans.

Currently, the methods for synthesis of N-alkylated morphinans known in the art have at least one of two primary limitations: (a) their dependence on a transition metal catalyst, and (b) the use of hydrogen gas as a source of hydrogen for the alkylation. Transition metal catalysts are expensive and toxic, which requires testing of the finished product to ensure that the final product does not contain more than a specified parts per million of the transition metal. Additionally, hydrogen gas is hazardous, and methods of synthesis typically employ high pressures. Some prior art methods have incorporated a borohydride to catalyze the reaction. It was desired to avoid this method because the side products are difficult to separate from the desired product, and the reactions may require lower temperatures, −20° to −30° C., when a keto group is present. In light of the current limitations, there is a need for an efficient, cost-effective method of the synthesis of N-alkylated normorphinans.

SUMMARY OF THE INVENTION

The present invention provides processes for the synthesis of N-alkylated morphinans from the corresponding normorphinan compounds.

One aspect of the present invention encompasses a process for the preparation of an N-alkylated morphinan. The method comprises contacting a normorphinan comprising a secondary amine at position 17 with an alkylating agent comprising $R^{10}$, wherein $R^{10}$ is selected from the group consisting of hydrocarbyl and substituted hydrocarbyl, a proton acceptor, and a reducing agent selected from the group consisting of formic acid, methyl formate, formamide, a mixture of formic acid and an alkali salt of formic acid, and combinations thereof, to form the N-alkylated morphinan comprising $NR^{10}$ at position 17.

In an additional aspect, the current invention encompasses a process for the preparation of a compound comprising Formula (IIIa). The process comprises: (a) contacting a compound comprising Formula (Ia) with an alkylating agent comprising $R^{10}$ in the presence of a proton acceptor to form a compound comprising Formula (IIa); and (b) contacting the compound comprising Formula (IIa) with a reducing agent selected from the group consisting of formic acid, methyl formate, formamide, a mixture of formic acid and an alkali salt of formic acid, and combinations thereof, to form a compound comprising Formula (IIIa) according to the following reaction scheme:

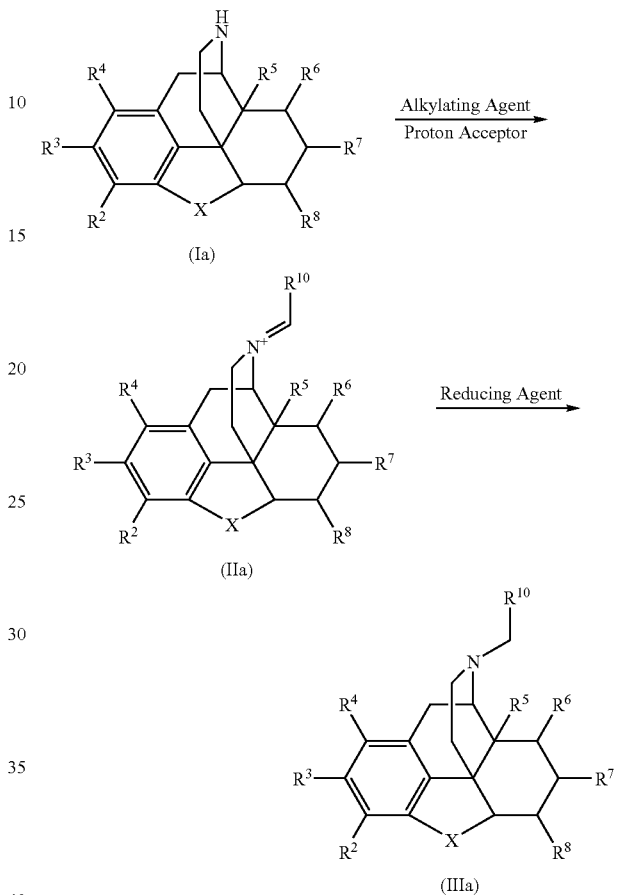

wherein:
- $R^2$, $R^6$, and $R^7$ are independently selected from the group consisting of hydrogen, hydrocarbyl, substituted hydrocarbyl, and $\{-\}OR^{11}$;
- $R^3$, and $R^4$ are independently selected from the group consisting of hydrogen, hydrocarbyl, substituted hydrocarbyl, halogen, and $\{-\}OR^{11}$;
- $R^5$ is selected from the group consisting of hydrogen, and hydroxyl;
- $R^8$ is selected from the group consisting of $\{=\}O$, and hydroxyl;
- $R^{10}$ is selected from the group consisting of hydrocarbyl, and substituted hydrocarbyl;
- $R^{11}$ is selected from the group consisting of hydrogen, hydrocarbyl, substituted hydrocarbyl, and a hydroxyl protecting group; and
- X is selected from the group consisting of oxygen and sulfur.

In another aspect the current invention encompasses a process for the preparation of a compound comprising Formula (IIIb). The process comprises: (a) contacting a compound comprising Formula (Ib) with an alkylating agent comprising $R^{10}$ in the presence of a proton acceptor to form a compound comprising Formula (IIb); and (b) contacting the compound comprising Formula (IIb) with a reducing agent selected from the group consisting of formic acid, methyl formate, formamide, a mixture of formic acid and an alkali salt of formic acid, and combinations thereof, to form a compound comprising Formula (IIIb) according to the following reaction scheme:

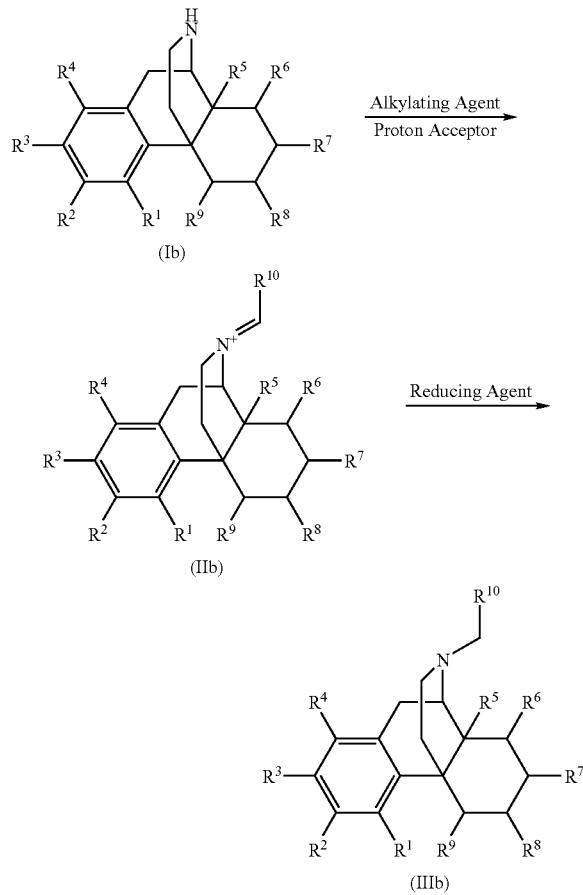

wherein:
$R^1$, $R^2$, $R^6$, $R^7$, and $R^9$ are independently selected from the group consisting of hydrogen, hydrocarbyl, substituted hydrocarbyl, and {—}$OR^{11}$;
$R^3$, and $R^4$ are independently selected from the group consisting of hydrogen, hydrocarbyl, substituted hydrocarbyl, halogen, and {—}$OR^{11}$;
$R^5$ is selected from the group consisting of hydrogen, and hydroxyl;
$R^8$ is selected from the group consisting of {=}O, and hydroxyl;
$R^{10}$ is selected from the group consisting of hydrocarbyl, and substituted hydrocarbyl; and
$R^{11}$ is selected from the group consisting of hydrogen, hydrocarbyl, substituted hydrocarbyl, and a hydroxyl protecting group.

DETAILED DESCRIPTION

The present invention provides an efficient process for the production of N-alkylated morphinans in high yield. In particular, the process of the present invention avoids the use of toxic metal catalysts and dangerous hydrogen gas. Moreover, the process of the invention may be conducted in a one-pot process, without isolation or purification of the intermediate products.

(a) Process for the Synthesis of N-Alkylated Morphinans

One aspect of the present invention provides an efficient process for the production of N-alkylated morphinan compounds. The process comprises contacting a normorphinan comprising a secondary amine at position 17 with an alkylating agent comprising $R^{10}$, wherein $R^{10}$ is selected from the group consisting of hydrocarbyl and substituted hydrocarbyl, a proton acceptor, and a reducing agent selected from the group consisting of formic acid, methyl formate, formamide, a mixture of formic acid and an alkali salt of formic acid, and combinations thereof to form the N-alkylated morphinan comprising $NR^{10}$ at position 17.

Generally, the normorphinan comprises any compound having a morphinan structure, in which the nitrogen at position 17 comprises a secondary amine. It will be understood by one skilled in the art that the "nor" compound may be produced by methods known in the art or purchased as a starting material. Non-limiting examples of normorphinans include norcodeine, normorphine, northebaine, nororipavine, noroxymorphone, nordihydromorphine, nordihydrocodeine, norhydrocodone, norhydromorphone, noroxycodone, nordextromethorphan, nordextrorphan, norlevomethorphan, norlevorphanol, norbuprenorphine, noroxymomorphol, noroxycodol norsinomenine, nordihydrosinomnine, and combinations thereof. In a preferred embodiment, the normorphinan comprises noroxymorphone.

The N-alkylated morphinan comprises any morphinan compound comprising a tertiary amine at position 17, wherein the amine at position 17 comprises a hydrocarbyl or substituted hydrocarbyl group. Suitable examples of N-alkylated morphinans include, but are not limited to codeine, morphine, thebaine, oripavine, oxymorphone, dihydromorphone, dihydrocodeine, hydrocodone, hydromorphone, oxycodone, oxycodeinone, naloxone, naltrexone, nalbuphine, nalmefene, nalfurafine, morphinone, ethylmorphine, butorphanol, dextromethorphan, dextrorphan, levomethorphan, levorphanol, buprenorphine, sinomenine, dihydrosinomenine, and combinations thereof. In a preferred embodiment, the N-alkylated morphinan comprises naltrexone, nalbuphine, or 6-ketonalbuphine.

In general, the $R^{10}$ group used to alkylate the nitrogen at position 17 is a hydrocarbyl or substituted hydrocarbyl group. In a preferred embodiment, the $R^{10}$ group may be an alkyl, cycloalkyl, cycloalkylmethyl, alkenyl, alkynyl, or aryl group. In an exemplary embodiment, the $R^{10}$ group may be methyl, cyclopropylmethyl, cyclobutylmethyl, or allyl.

The process comprises formation of an intermediate compound comprising an iminium salt of the normorphinan compound, prior to the formation of the N-alkylated morphinan. The iminium salt serves as the substrate for reduction by formic acid, methyl formate, formamide, a mixture of formic acid and an alkali salt of formic acid, or combinations thereof, thereby forming the N-alkylated morphinan. The iminium salt is generally considered a protonated or substituted imine compound comprising the formula $N^+=CR^{10}$ at position 17, wherein $R^{10}$ is a hydrocarbyl or substituted hydrocarbyl group as defined above. In a preferred embodiment, the $R^{10}$ group of iminium salt may be an alkyl, cycloalkyl, cycloalkylmethyl, alkenyl, alkynyl, or aryl group. In an exemplary embodiment, the $R^{10}$ group may be methyl, cyclopropylmethyl, cyclobutylmethyl, or allyl.

(b) Synthesis of Compounds Comprising Formula (IIIa)

In one embodiment, an N-alkylated morphinan comprising Formula (IIIa) is synthesized from a normorphinan comprising Formula (Ia). For purposes of illustration, Reaction Scheme 1 depicts the production of the compound comprising Formula (IIIa) in accordance with one aspect of the present invention:

Reaction Scheme 1:

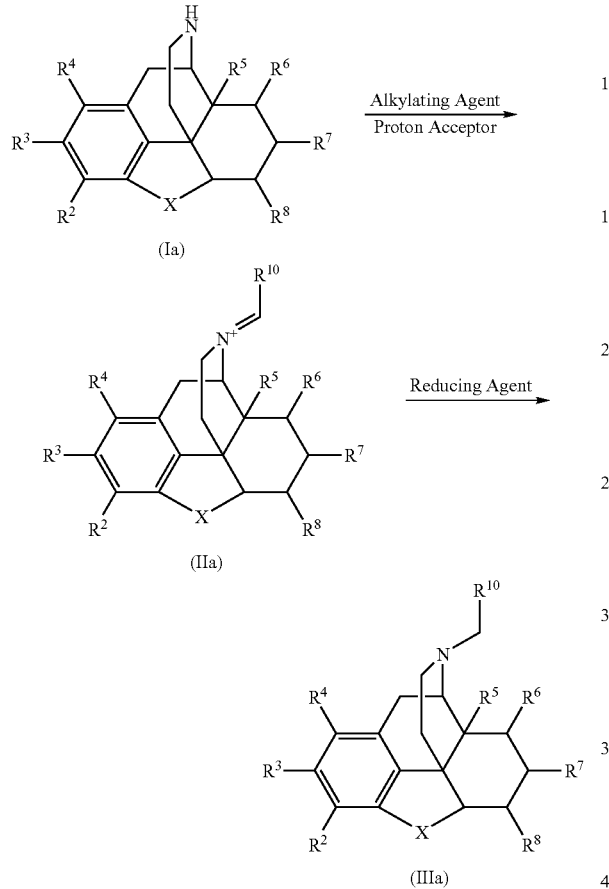

wherein:
- $R^2$, $R^6$, and $R^1$ are independently selected from the group consisting of hydrogen, hydrocarbyl, substituted hydrocarbyl, and $\{-\}OR^{11}$;
- $R^3$, and $R^4$ are independently selected from the group consisting of hydrogen, hydrocarbyl, substituted hydrocarbyl, halogen, and $\{-\}OR^{11}$;
- $R^5$ is selected from the group consisting of hydrogen, and hydroxyl;
- $R^8$ is selected from the group consisting of $\{=\}O$, and hydroxyl;
- $R^{10}$ is selected from the group consisting of hydrocarbyl, and substituted hydrocarbyl;
- $R^{11}$ is selected from the group consisting of hydrogen, hydrocarbyl, substituted hydrocarbyl, and a hydroxyl protecting group; and
- X is selected from the group consisting of oxygen and sulfur.

In preferred iterations, $R^3$, $R^4$, $R^6$, and $R^7$ are each hydrogen and X is oxygen. $R^2$ is preferably $\{-\}OR^{11}$, wherein $R^{11}$ is selected from the group consisting of hydrogen, hydrocarbyl, substituted hydrocarbyl, and a hydroxyl protecting group. $R^5$ is preferably hydroxyl. $R^8$ is preferably $\{=\}O$. Furthermore, $R^{10}$ is preferably alkyl, cycloalkyl, cycloalkylmethyl, allyl, or aryl; or more preferably methyl, allyl, cyclopropylmethyl, or cyclobutylmethyl. In one exemplary embodiment, $R^3$, $R^4$, $R^6$, and $R^7$ are each hydrogen, X is oxygen, $R^2$ is hydroxyl, $R^5$ is $\{-OH\}$, $R^8$ is $\{=\}O$, and $R^{10}$ is cyclopropylmethyl. In another exemplary embodiment, $R^3$, $R^4$, $R^6$, and $R^7$ are each hydrogen, X is oxygen, $R^2$ is $\{-\}OH$, $R^5$ is $\{-\}OH$, $R^8$ is $\{=\}O$, and $R^{10}$ is cyclobutylmethyl.

Representative compounds comprising Formula (IIIa) include, but are not limited to oxymorphone, dihydromorphone, hydrocodone, hydromorphone, oxycodone, oxycodeinone, naloxone, naltrexone, nalbuphine, nalmefene.

(c) Synthesis of Compound Comprising Formula (IIIb)

In an additional embodiment, an N-alkylated morphinan comprising Formula (IIIb) is synthesized from a normorphinan comprising Formula (Ib). For purposes of illustration, Reaction Scheme 2 depicts the production of the compound comprising Formula (IIIb) in accordance with one aspect of the present invention:

Reaction Scheme 2:

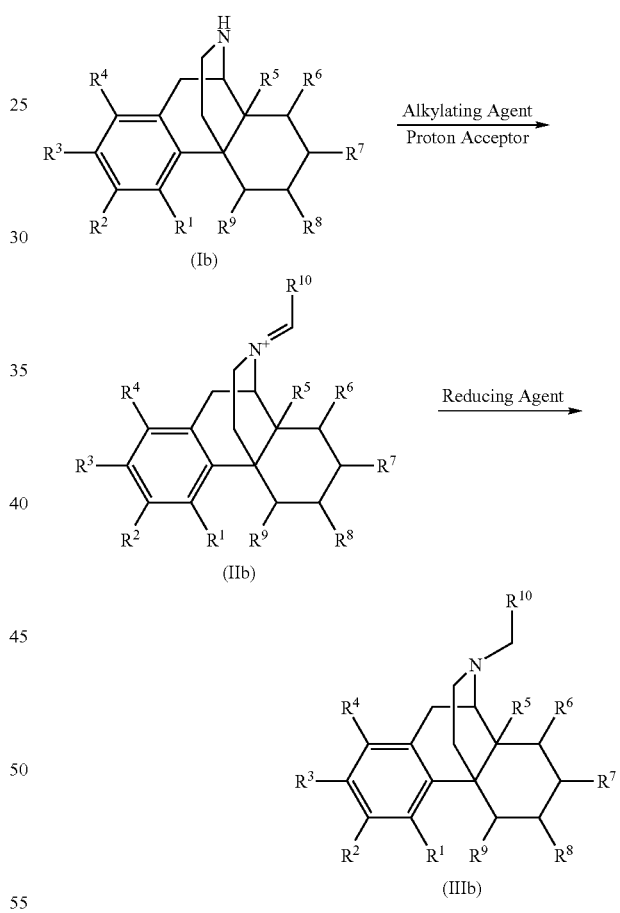

wherein:
- $R^1$, $R^2$, $R^6$, $R^7$, and $R^9$ are independently selected from the group consisting of hydrogen, hydrocarbyl, substituted hydrocarbyl, and $\{-\}OR^{11}$;
- $R^3$, and $R^4$ are independently selected from the group consisting of hydrogen, hydrocarbyl, substituted hydrocarbyl, halogen, and $\{-\}OR^{11}$;
- $R^5$ is selected from the group consisting of hydrogen, and hydroxyl;
- $R^8$ is selected from the group consisting of $\{=\}O$, and hydroxyl;

$R^{10}$ is selected from the group consisting of hydrocarbyl, and substituted hydrocarbyl; and $R^{11}$ is selected from the group consisting of hydrogen, hydrocarbyl, substituted hydrocarbyl, and a hydroxyl protecting group.

In preferred embodiments, $R^3$, $R^4$, and $R^6$ are each hydrogen. Additionally, $R^1$ is preferably hydrogen or hydroxyl. $R^2$ is preferably {—}$OR^{11}$, wherein $R^{11}$ is selected from the group consisting of hydrogen, hydrocarbyl, substituted hydrocarbyl, and a hydroxyl protecting group. $R^7$ is preferably hydrogen or {—}$OR^{11}$. $R^8$ is preferably hydroxyl or {=}O. $R^{10}$ is preferably alkyl, cycloalkyl, cycloalkylmethyl, allyl, or aryl; or more preferably methyl, allyl, cyclopropylmethyl, or cyclobutylmethyl.

Representative compounds comprising Formula (IIIb) include, but are not limited to butorphanol, dextromethorphan, dextrorphan, levomethorphan, and levorphanol.

(d) Reaction Mixture

The process of the invention commences with formation of a reaction mixture by combining the compound comprising Formulas (Ia) or (Ib) with an alkylating agent in the presence of a proton acceptor. A variety of alkylating agents are suitable for use in the process of the invention. Generally, the alkylating agent transfers an alkyl group from the alkylating agent to the nitrogen at position 17 of the normorphinan, and can therefore be thought of as any compound capable of transferring an alkyl group. In a preferred embodiment, the alkylating agent may be an aldehyde, having the general formula $R^{10}$CHO, wherein $R^{10}$ may be hydrocarbyl or substituted hydrocarbyl. In preferred embodiments, $R^{10}$ may be alkyl, substituted alkyl, cycloalkyl, substituted cycloalkyl, cycloalkylmethyl, alkenyl, alkynyl, aryl, cyclopropylmethyl, cyclobutylmethyl, or allyl. Examples of aldehydes that may be used include, but are not limited to alkyl-aldehydes such as methanal, ethanal, propanal, substituted propanal, butanal, substituted butanal, pentanal, substituted pentanal, hexanal, substituted hexanal, heptanal, substituted heptanal, octanal, substituted octanal, nonanal, substituted nonanal, decanal, substituted decanal, undecanal, substituted undecanal, dodecanal, substituted dodecanal, and substituted variations thereof; cycloalkyl-aldehydes such as cyclopropanecarboxaldehyde, cyclobutanecarboxaldehyde, cyclopentanecarboxaldehyde, cyclohexancarboxaldehyde, cycloheptanecarboxaldehyde, cyclooctanecarboxaldehyde, cyclononanecarboxaldehyde, cyclodecanecarboxaldehyde, benzalaldehyde, cinnamaldehyde, tolualdehyde (4-methylbenzaldehyde), and substituted variations thereof; and aldehydes having two terminal carbonyl groups such as ethanedial, propanedial, butanedial, pentanedial, hexanedial, heptanedial, octanedial, nonanedial, decanedial, undecanedial, dodecanedial, and substituted variations thereof. In a preferred embodiment, the alkylating agent may be cyclopropanecarboxaldehyde or cyclobutanecarboxaldehyde.

The mole-to-mole ratio of the compound comprising Formulas (Ia) or (Ib) to the alkylating agent can and will vary. In general, the mole-to-mole ratio of the compound comprising Formulas (Ia) or (Ib) to the alkylating agent may range from about 1:0.5 to about 1:5. In a preferred embodiment, the ratio of compound comprising Formulas (Ia) or (Ib) to the alkylating agent may range from about 1:1 to about 1:2. In an exemplary embodiment, the mole-to-mole ratio of the compound comprising Formulas (Ia) or (Ib) to the alkylating agent may be about 1:1.4.

The process of this invention additionally requires an agent for reducing the intermediate compound comprising Formula (IIa) or (IIb). In general, the reducing agent will be formic acid, an ester of formic acid, an alkali salt of formic acid, formamide, mixtures of formic acid and a salt of formic acid, or any combination thereof. Suitable esters of formic acid include but are not limited to methyl formate, ethyl formate, trimethyl formate, triethyl formate, methyl chloroformate, and the like. Non-limiting examples of suitable alkali salts of formic acid include sodium formate, lithium formate, potassium formate, and cesium formate. In an exemplary embodiment, the reducing agent may be formic acid.

Generally, the mole-to-mole ratio of the compound comprising Formula (Ia) or (Ib) to the reducing agent will range from about 1:1 to about 1:20. In a preferred embodiment, the mole-to-mole ratio of the compound comprising Formula (Ia) or (Ib) to the reducing agent may range from about 1:10 to about 1:15. In an exemplary embodiment, the mole-to-mole ratio of the compound comprising Formula (Ia) or (Ib) to the reducing agent may be about 1:12.

The process of this invention is also conducted in the presence of a proton acceptor. In general, the proton acceptor has a pKa of between about 7 and about 13, preferably between about 8 and about 10. Representative proton acceptors that may be employed include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), alkyl amine bases (such as, for example, triethylamine, trimethylamine, tributylamine, diethylamine, and diisopropylethylamine), organic bases (such as, for example, pyridine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino) ethanesulfonic acid (CHES), 4-(2-hydroxyethyl)-1-piperazinepropanesulfonic acid (EPPS), 4-(2-hydroxyethyl) piperazine-1-ethanesulfonic acid (HEPES), 2-(4-morpholinyl) ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. In a preferred embodiment, the proton acceptor may be triethylamine, trimethylamine, tributylamine, or pyridine. In an exemplary embodiment, the proton acceptor may be triethylamine. The mole-to-mole ratio of the compound comprising Formula (Ia) or (Ib) to the proton acceptor may range from about 1:1 to about 1:20. In a preferred embodiment, the mole-to-mole ratio of the compound comprising Formula (Ia) or (Ib) to the proton acceptor may range from about 1:5 to about 1:10. In an exemplary embodiment, the mole-to-mole ratio of the compound comprising Formula (Ia) or (Ib) to the proton acceptor may be about 1:8.

In addition, the process of this invention is generally conducted in the presence of a solvent. The solvent may be a protic solvent, an aprotic solvent, or an organic solvent. Suitable examples of protic solvents include, but are not limited to, methanol, ethanol, isopropanol, n-propanol, isobutanol, n-butanol, s-butanol, t-butanol, formic acid, acetic acid, water, and combinations thereof. Non-limiting examples of suitable aprotic solvents include acetone, acetonitrile, diethoxymethane, N,N-dimethylformamide (DMF), dimethyl sulfoxide (DMSO), N,N-dimethylpmpionamide, 1,3- dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), 1,4-dioxane, N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), 2-methyl tetrahydrofuran, toluene, trichloromethane, and combinations thereof. Suitable examples of organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, diethylene glycol, fluorobenzene, heptane, hexane, isobutylmethylketone, isopropyl acetate, methylethylketone, methyltetrahydrofuran, pentyl acetate, n-propyl acetate, tetrahydrofuran, toluene, and combinations thereof. In a preferred embodiment, the solvent may be the protic solvent methanol. In general, the weight ratio of the solvent to the compound comprising Formula (Ia) or (Ib) will range from about 0.5:1 to about 100:1. In preferred embodiments, the weight ratio of the solvent to the compound comprising Formula (Ia) or (Ib) may range from about 2:1 to about 5:1.

(e) Reaction Conditions

In general, the reaction may be conducted at a temperature that ranges from about 20° C. to about 120° C. for a period of time that is sufficient to convert a substantial portion of the compound comprising Formula (Ia) or (Ib) to the compound comprising Formula (IIIa) or (IIIb). In a preferred embodiment, the reaction may be conducted at a temperature that ranges from about 40° C. to about 100° C. In an exemplary embodiment, the reaction may be conducted at a temperature that ranges from about 50° C. to about 80° C.

Typically, the reaction is allowed to proceed for a sufficient period of time until the reaction is complete, as determined by any method known to one skilled in the art, such as chromatography (e.g., HPLC). In this context, a "completed reaction" generally means that the reaction mixture contains a significantly diminished amount of the compound comprising Formula (Ia) or (Ib) and a significantly increased amount of the compound comprising Formula (IIIa) or (IIIb) compared to the amounts of each present at the beginning of the reaction. Typically, the amount of the compound comprising Formula (Ia) of (Ib) remaining in the reaction mixture may be less than about 3%, and preferably less than about 1%.

The yield of the compound comprising Formula (IIIa) or (IIIb) can and will vary. Typically, the yield of the compound comprising Formula (IIIa) or (IIIb) may be at least about 50%. In preferred embodiments of the invention, the yield of the compound comprising Formula (IIIa) or (IIIb) may be at least about 65%.

The reaction may also be performed in a one-pot process, whereby all reagents are added in one step to form the reaction mixture. Accordingly, the reaction mixture comprises the compound comprising Formula (Ia) or (Ib), the alkylating agent, the proton acceptor, and the reducing agent, as defined above. The one-pot process of the invention substantially eliminates the need to isolate or purify the intermediate compound comprising Formula (IIa) or (IIb) and/or to manually add the reducing agent to the reaction mixture upon completion of the reaction with the alkylating reagent.

(f) Stereochemistry and Enantiomers

Any of the compounds comprising any of Formulas (I) or (II) may have a (−) or (+) orientation with respect to the rotation of polarized light, based on whether the starting material used is in the (−) or (+) opiate absolute form. More specifically, each chiral center may have an R or an S configuration. The compounds formed by the processes of the invention comprise morphinans. For purposes of illustration, the carbon atoms of a morphinan compound are numbered as diagrammed below.

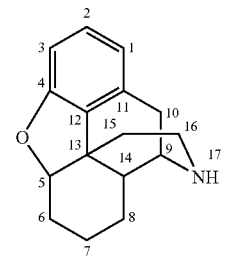 [SMILES: c1cc2c3c(c1)OC1CCCC4C(C2)NCCC314]

These morphinan compounds are recognized to have an alpha face and a beta face. Some compounds described herein, may have at least three chiral centers, namely carbons C13, C14, and C9, provided that the C15 and C16 atoms are both on the alpha face of the molecule or both on the beta face of the molecule. Additionally, if the compound comprises a heterocyclic ring between carbons C4 and C5, C5 may also be a chiral center. At each chiral center, the stereochemistry at the carbon atom is independently R or S.

Some compounds described herein, such as compounds comprising Formula (Ia), (IIa) and (IIIa), may have at least four chiral centers, namely carbons C5, C9, C13, and C14. At each chiral center, the stereochemistry at the carbon atom is independently R or S. The configuration of carbons 5, 13, 14, and 9, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C15 and C16 atoms are both on the alpha face of the molecule or both on the beta face of the molecule. Additionally, the nitrogen at position 17 may be either R or S, and depending on the R8 group chosen, C6 may also be a chiral center, with a stereochemistry of either R or S.

Additional compounds described herein, such as compounds comprising Formula (Ib), (IIb), and (IIIb), may have at least three chiral centers, namely carbons C13, C14, and C9. At each chiral center, the stereochemistry at the carbon atom is independently R or S. The configuration of carbons 13, 14, and 9, respectively, may be RRR, RRS, RSR, SRR, SRS, SSR, RSS, or SSS, provided that the C15 and C16 atoms are both on the alpha face of the molecule or both on the beta face of the molecule. Additionally, the nitrogen at position 17 may be either R or S, and depending on the R8 group chosen, C6 may also be a chiral center, with a stereochemistry of either R or S.

DEFINITIONS

To facilitate understanding of the invention, several terms are defined below:

The compounds described herein may have asymmetric centers. Compounds of the present invention containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O), wherein R is $R^1$, $R^1O—$, $R^1R^2N—$, or $R^1S—$, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocycle" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocycle group preferably has 1 or 2 oxygen atoms and/or 1 to 4 nitrogen atoms in the ring, and is bonded to the remainder of the molecule through a carbon or heteroatom. Exemplary heterocycle groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amide, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom, wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of Naltrexone

A quantity of 0.50 grams noroxymorphone was placed within a test tube. A stir bar was added to the test tube, which was subsequently sealed with a rubber septum. Subsequently, 1.0 mL methanol was added to the test tube to create a reaction mixture. Next, 1.0 mL of methanol was mixed with 2.0 mL of triethylamine in a separate test tube, and the mixture was chilled in an ice bath. After the mixture was allowed to chill, 0.83 mL formic acid was added to the methanol and triethylamine mixture. During addition of formic acid, care was taken to ensure that the temperature of the mixture was less than 30° C. After addition of formic acid, 0.19 mL cyclopropanecarboxaldehyde (CPCA) was added to the mixture, with care to ensure that the temperature was maintained below 25° C.

Once the separate reaction mixture comprising methanol, triethylamine, formic acid, and CPCA mixture was formed, the mixture was added to the test tube containing the noroxymorphone and methanol mixture at a temperature of approximately 8° C. The combined reaction mixture was then heated by means of a J-Kem Personal Reaction Station (PRS) under an inert nitrogen environment. The temperature of the heating block was 74° C., but the internal temperature of the reaction mixture was measured at 72° C. Additionally, the temperature of the upper block was chilled to 0° C., and the reaction mixture was allowed to react.

After three hours, the reaction mixture was removed from heating and a sample was taken. Approximately one drop of the reaction mixture was placed in 0.5 mL of 1% acetic acid, to prepare a sample for verification of reaction product. Upon sample analysis, it was shown to have a mass recovery of approximately 96%. Testing by high performance liquid chromatography (HPLC) revealed a naltrexone concentration of approximately 73% (w/w) of the sample, resulting in a yield of approximately 70%.

Once the production of naltrexone was verified by the sample, 4.0 mL of water was added to the remaining reaction mixture. The reaction mixture was cooled to approximately 10° C. in an ice bath and the pH was adjusted to approximately 9, using concentrated ammonium hydroxide. The product was then extracted using 8 mL of dichloromethane. The product-containing layer was then separated and the product was further extracted with 3 mL dichloromethane. Subsequently, the product plus additional organic extracts were gathered and washed with 2 mL water. The organic extracts were filtered through cotton and concentrated on a rotary evaporator (rotovap) to create a foamy yellow solid, weighing approximately 0.592 grams. Next, the vial containing the reaction product was placed in a vacuum oven at ambient temperature under approximately 40 mm Hg vacuum pressure to further dry the sample. After approximately 19 hours in the vacuum oven, the sample was removed resulting in a tan solid weighing approximately 0.570 grams, which was subsequently verified to be naltrexone by HPLC assay.

Thus, 0.50 grams of noroxymorphone was reacted according to the process described above to produce 0.570 grams naltrexone.

Example 2

Production of 6-Ketonalbuphine

A quantity of 0.50 grams noroxymorphone was placed within a test tube. A stir bar was added to the test tube, which was subsequently sealed with a rubber septum. Subsequently, 1.0 mL methanol was added to the test tube to create a reaction mixture. Next, 1.0 mL of methanol was mixed with 2.0 mL of triethylamine in a separate test tube, and the mixture was chilled in an ice bath. After the mixture was allowed to chill, 0.83 mL formic acid was added to the methanol and triethylamine mixture. During addition of formic acid, care was taken to ensure that the temperature of the mixture was less than 30° C. After addition of formic acid, 0.19 mL cyclobutanecarboxaldehyde (CBCA) was added to the mixture, with care to ensure that the temperature was maintained below 25° C.

Once the separate reaction mixture comprising methanol, triethylamine, formic acid, and CBCA mixture was formed, the mixture was added to the test tube containing the noroxymorphone and methanol mixture at a temperature of approximately 8° C. The combined reaction mixture was then heated by means of a J-Kem Personal Reaction Station (PRS) under an inert nitrogen environment. The temperature of the heating block was 74° C., but the internal temperature of the reaction mixture was measured at 72° C. Additionally, the temperature of the upper block was chilled to 0° C., and the reaction mixture was allowed to react.

After three hours, the reaction mixture was removed from heating and a sample was taken. Approximately one drop of the reaction mixture was placed in 0.5 mL of 1% acetic acid, to prepare a sample for verification of reaction product. Upon analysis, the sample was shown to have a mass recovery of approximately 108%. Testing by high performance liquid chromatography (HPLC) revealed a 6-ketonalbuphine concentration of approximately 77% (w/w) of the sample, resulting in a yield of approximately 83%.

Once the production of 6-ketonalbuphine was verified, 4.0 mL of water was added to the remaining reaction mixture. The reaction mixture was cooled to approximately 10° C. in an ice bath and the pH was adjusted to approximately 9, using concentrated ammonium hydroxide. The product was then extracted using 8 mL of dichloromethane. The product-containing layer was then separated and the product was further extracted with 3 mL dichloromethane. Subsequently, the product plus additional organic extracts were gathered and washed with 2 mL water. The organic extracts were filtered through cotton and concentrated on a rotary evaporator (rotovap) to create a foamy tan solid, weighing approximately 0.685 grams. Next, the vial containing the reaction product was placed in a vacuum oven at ambient temperature under approximately 40 mm Hg vacuum pressure to further dry the sample. After approximately 19 hours in the vacuum oven, the sample was removed resulting in a tan solid weighing approximately 0.666 grams, which was subsequently verified to be 6-ketonalbuphine by HPLC assay.

Thus, 0.50 grams of noroxymorphone was reacted according to the process described above to produce 0.666 grams 6-ketonalbuphine.

What is claimed is:

1. A process for the preparation of an N-alkylated morphinan having $NR^{10}$ at position 17, the process comprising contacting a normorphinan having a secondary amine at position 17 with an alkylating agent having $R^{10}$, wherein $R^{10}$ is chosen from hydrocarbyl and substituted hydrocarbyl, a proton acceptor, and a reducing agent chosen from formic acid, methyl formate, formamide, a mixture of formic acid and an alkali salt of formic acid, and combinations thereof to form the N-alkylated morphinan having $NR^{10}$ at position 17, wherein the process occurs without the use of a transition metal catalyst.

2. The process of claim 1, wherein the reaction forming the N-alkylated morphinan having $NR^{10}$ at position 17 is conducted in a one-pot process.

3. The process of claim 1, wherein the normorphinan is chosen from norcodeine, normorphine, northebaine, nororipavine, noroxymorphone, nordihydromorphine, nordihydrocodeine, norhydrocodone, norhydromorphone, noroxycodone, nordextromethorphan, nordextrorphan, norlevomethorphan, norlevorphanol, norbuprenorphine, noroxymomorphol, noroxycodol, norsinomenine, and nordihydrosinomenine; the N-alkylated morphinan is chosen from codeine, morphine, thebaine, oripavine, oxymorphone, dihydromorphone, dihydrocodeine, hydrocodone, hydromorphone, oxycodone, oxycodeinone, naloxone, naltrexone, nalbuphine, nalmefene, nalfurafine, morphinone, ethylmorphine, butorphanol, dextromethorphan, dextrorphan, levomethorphan, levorphanol, buprenorphine, sinomenine, and dihydrosinomenine; the alkylating agent is an aldehyde; and $R^{10}$ is chosen from alkyl, cycloalkyl, cycloalkylmethyl, alkenyl, alkynyl, and aryl.

4. The process of claim 1, wherein the normorphinan is chosen from norcodeine, normorphine, northebaine, noroxymorphone, nordihydromorphine, nordihydrocodeine, norhydrocodone, norhydromorphone, noroxycodone, nordextromethorphan, nordextrorphan, norlevomethorphan, norlevorphanol, norsinomenine, and nordihydrosinomenine; the proton acceptor is triethylamine; the alkylating agent is an aldehyde, and $R^{10}$ is chosen from alkyl, cycloalkyl, cycloalkylmethyl, alkenyl, alkynyl, and aryl.

5. The process of claim 1, wherein an intermediate compound of an iminium salt of the normorphinan is formed in the reaction prior to the formation of the N-alkylated morphinan.

6. The process of claim 5, wherein the N-alkylated morphinan is Formula (IIIa), the process comprising:

(a) contacting a compound of Formula (Ia) with the alkylating agent having $R^{10}$ in the presence of a proton acceptor to form a compound of Formula (IIa); and (b) contacting the compound of Formula (IIa) with the reducing agent chosen from formic acid, methyl formate, formamide, a mixture of formic acid and an alkali salt of formic acid, and combinations thereof, to form the compound of Formula (IIIa) according to the following reaction scheme:

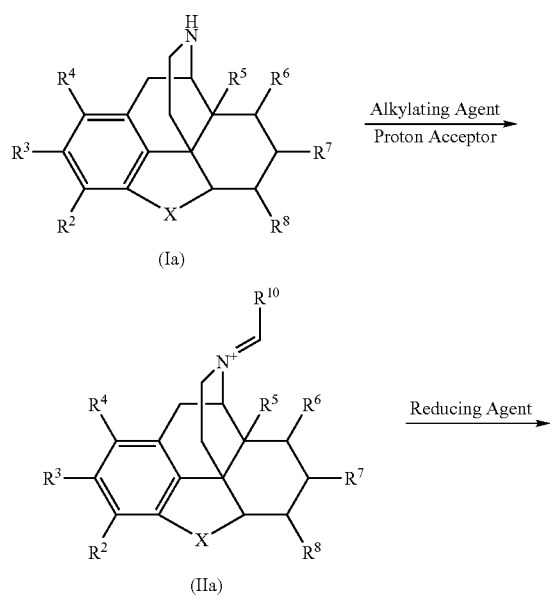

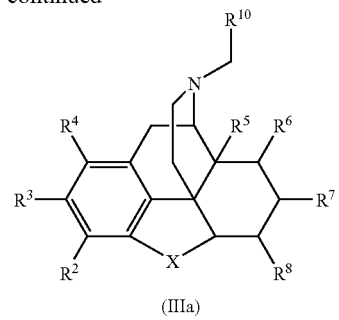

wherein:

$R^2$, $R^6$, and $R^7$ are independently chosen from hydrogen, hydrocarbyl, substituted hydrocarbyl, and $\{-\}OR^{11}$;

$R^3$, and $R^4$ are independently chosen from hydrogen, hydrocarbyl, substituted hydrocarbyl, halogen, and $\{-\}OR^{11}$;

$R^5$ is chosen from hydrogen, and hydroxyl;

$R^8$ is chosen from $\{=\}O$, and hydroxyl;

$R^{10}$ is chosen from hydrocarbyl, and substituted hydrocarbyl;

$R^{11}$ is chosen from hydrogen, hydrocarbyl, substituted hydrocarbyl, and a hydroxyl protecting group; and X is chosen from oxygen and sulfur.

7. The process of claim 6, wherein $R^3$, $R^4$, $R^6$, and $R^7$ are hydrogen, $R^8$ is $\{=\}O$, $R^{10}$ is a cycloalkyl group, and X is oxygen.

8. The process of claim 6, wherein $R^3$, $R^4$, $R^8$, and $R^7$ are hydrogen, $R^8$ is a hydroxyl group, $R^{10}$ is a cycloalkylmethyl group, and X is oxygen.

9. The process of claim 6, wherein the alkylating agent is an aldehyde of the formula $R^{10}CHO$, the reducing agent is formic acid, and the reaction is performed in the presence of a protic solvent.

10. The process of claim 6, wherein the proton acceptor is triethylamine; the alkylating agent is a carboxaldehyde, $R^{10}$ is selected from the group consisting of cyclopropylmethyl and cyclobutylmethyl; and the reaction is conducted in the presence of a protic solvent comprising an alcohol group.

11. The process of claim 6, wherein the reaction is conducted in a one-pot process.

12. The process of claim 6, wherein the optical activity of compounds of Formulas (Ia), (IIa), and (IIIa) is (−) or (+), and the configuration of carbons 5, 13, 14, and 9, respectively, is chosen from RRRR, RRRS, RRSR, RSRR, SRRR, RRSS, RSSR, SSRR, SRRS, SRSR, RSRS, RSSS, SRSS, SSRS, SSSR, and SSSS, provided that the carbons at positions 15 and 16 are both either on the alpha face of the molecule or the beta face of the molecule.

13. The process of claim 5, wherein the N-alkylated morphinan is Formula (IIIb), the process comprising:

(a) contacting a compound of Formula (Ib) with the alkylating agent having $R^{10}$ in the presence of a proton acceptor to form a compound of Formula (IIb); and (b) contacting the compound of Formula (IIb) with the reducing agent chosen from formic acid, methyl formate, formamide, a mixture of formic acid and an alkali salt of formic acid, and combinations thereof to form the compound comprising of Formula (IIIb) according to the following reaction scheme:

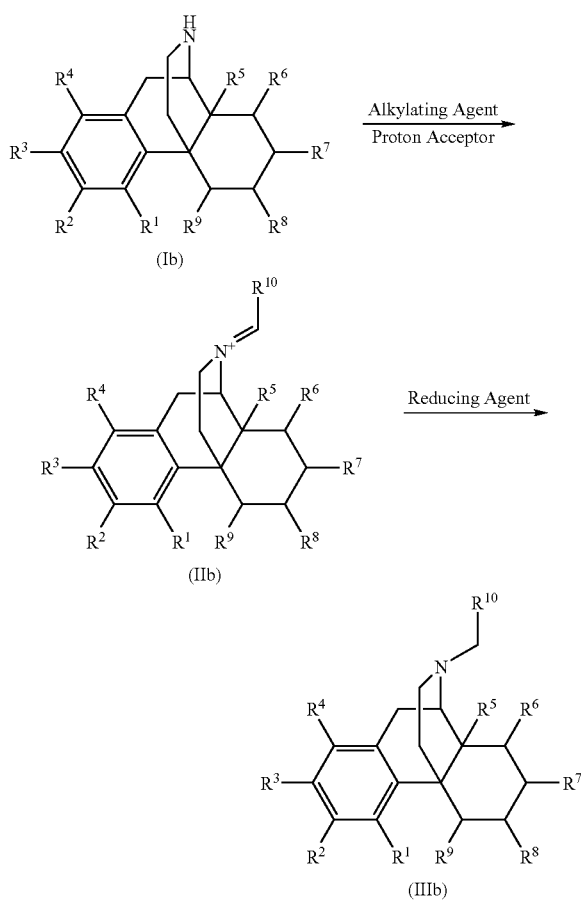

wherein:
R$^1$, R$^2$, R$^6$, and R$^7$, and R$^9$ are independently chosen from hydrogen, hydrocarbyl, substituted hydrocarbyl, and {—}OR$^{11}$;

R$^3$, and R$^4$ are independently chosen from hydrogen, hydrocarbyl, substituted hydrocarbyl, halogen, and {—}OR$^{11}$;

R$^5$ is chosen from hydrogen, and hydroxyl;

R$^8$ is chosen from {=}O, and hydroxyl;

R$^{10}$ is chosen from hydrocarbyl, and substituted hydrocarbyl; and

R$^{11}$ is chosen from hydrogen, hydrocarbyl, substituted hydrocarbyl, and a hydroxyl protecting group.

14. The process of claim 13, wherein R$^1$, R$^3$, R$^4$, R$^6$, R$^7$, and R$^9$ are hydrogen, R$^8$ is {=}O, and R$^{10}$ is a cycloalkyl group.

15. The process of claim 13, wherein R$^1$, R$^3$, R$^4$, R$^6$, R$^7$, and R$^9$ are hydrogen, R$^8$ is a hydroxyl group, and R$^{10}$ is a cycloalkylmethyl group.

16. The process of claim 13, wherein the alkylating agent is an aldehyde of the formula R$^{10}$CHO, the reducing agent is formic acid, and the reaction is performed in the presence of a protic solvent.

17. The process of claim 13, wherein the proton acceptor is triethylamine; the alkylating agent is a carboxaldehyde, R$^{10}$ is chosen from cyclopropylmethyl and cyclobutylmethyl; and the reaction is conducted in the presence of a protic solvent comprising an alcohol group.

18. The process of claim 13, wherein the reaction is conducted in a one-pot process.

19. The process of claim 13, wherein the optical activity of compounds of Formulas (Ib), (IIb), and (IIIb) is (−) or (+) and the configuration of C13, C14, and C9, respectively, is chosen from RRR, RRS. RSR, SRR, SRS, SSR, RSS, and SSS, provided that the carbons at positions 15 and 16 are both either on the alpha face of the molecule or the beta face of the molecule.

20. The process of claim 1, wherein the process comprises forming an initial reaction mixture consisting of the normorphinan, the alkylating agent, the proton acceptor, the reducing agent and a solvent.

* * * * *